| United States Patent [19]
Borrelli et al.

[11] Patent Number: 4,574,782
[45] Date of Patent: Mar. 11, 1986

[54] RADIO FREQUENCY-INDUCED HYPERTHERMIA FOR TUMOR THERAPY

[75] Inventors: Nicholas F. Borrelli, Elmira; Albert A. Luderer, Corning; Gerald R. Mansfield, Painted Post, all of N.Y.; Joseph N. Panzarino, Northboro, Mass.

[73] Assignee: Corning Glass Works, Corning, N.Y.

[21] Appl. No.: 553,376

[22] Filed: Nov. 21, 1983

Related U.S. Application Data

[63] Continuation-in-part of Ser. No. 321,469, Nov. 16, 1981, abandoned.

[51] Int. Cl.$^4$ .............................................. A61B 17/52
[52] U.S. Cl. ....................................................... 128/1.3
[58] Field of Search ................. 128/1 R, 1.3, 260, 804

[56] References Cited

U.S. PATENT DOCUMENTS 4,323,056  4/1982  Borrelli ................................ 128/1.3
4,369,345  1/1983  Czerlinski ........................... 128/1.5

*Primary Examiner*—Peter D. Rosenberg
*Attorney, Agent, or Firm*—C. S. Janes, Jr.

[57] ABSTRACT

This invention is directed to a method for reducing the mass of a tumor in animal tissue utilizing localized, magnetically-coupled, RF-induced hyperthermia. The method involves the implanting of a material in and/or closely adjacent to the tumor which is non-toxic to, and preferably inert to and compatible with, normal tissue and which has encapsulated therewithin ferromagnetic particles of such size, amount, composition, and ferromagnetism to develop a heating value of up to about one watt/gram, through essentially only hysteresis heating, under an applied field of about 20 but less than 200 oersteds at a frequency greater than 10 kilohertz and ranging up to about 600 kilohertz, or under an applied field of at least about 2000 oersteds and a frequency below about 40 hertz. Such heating value is sufficient to kill the tumor cells but muscle and nerve response of the animal body to the induced emf is minimized.

11 Claims, 5 Drawing Figures

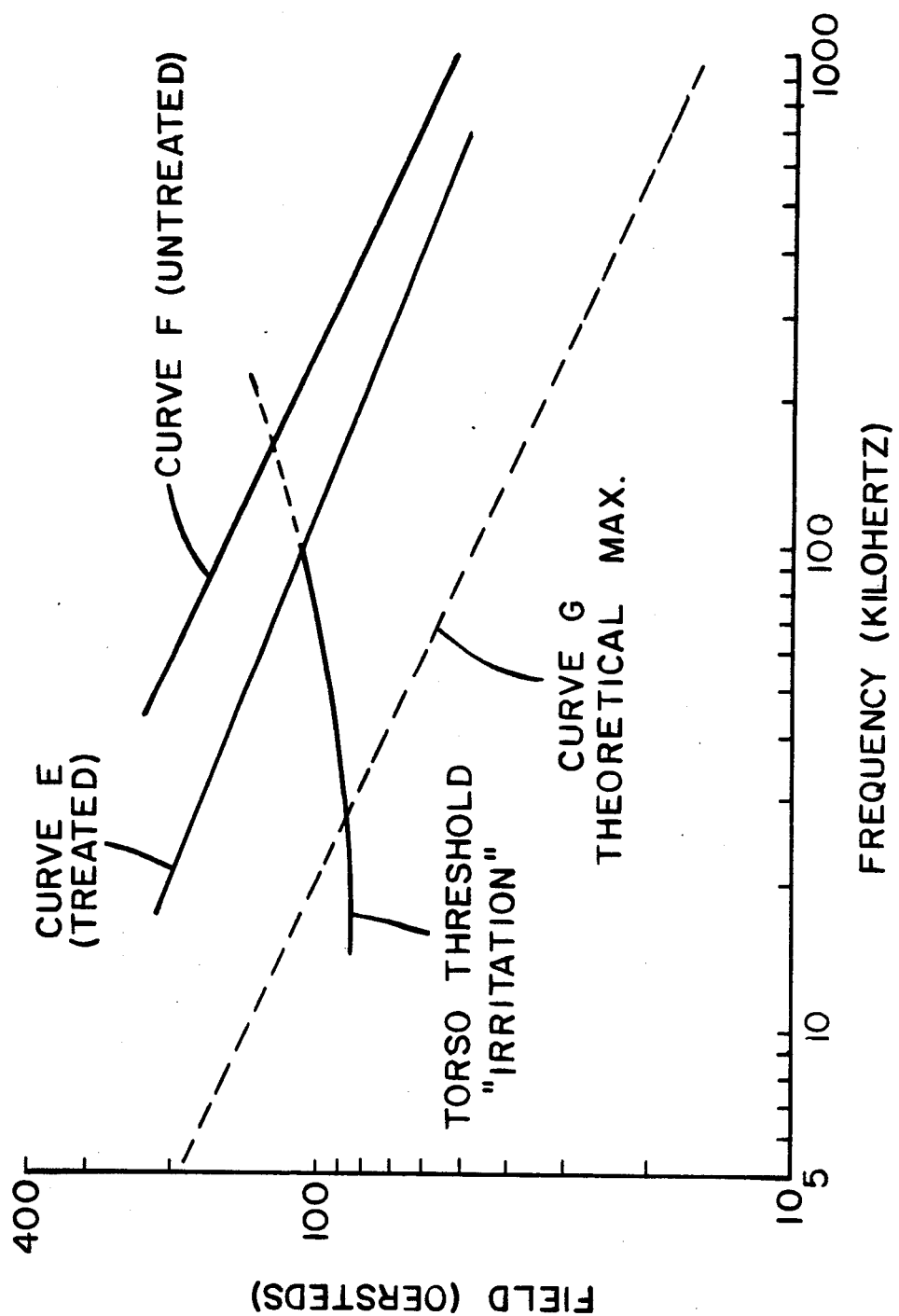

RADIO FREQUENCY-INDUCED HYPERTHERMIA FOR TUMOR THERAPY

This application is a continuation-in-part of application Ser. No. 321,469, filed Nov. 16, 1981, and now abandoned.

BACKGROUND OF THE INVENTION

U.S. application Ser. No. 151,210, filed May 19, 1980 in the names of N. F. Borrelli, A. A. Luderer, and J. N. Panzarino, now U.S. Pat. No. 4,323,056, discloses a tumor treatment modality which results in a reduction of tumor mass and may lead to complete eradication of a tumor. The inventive method comprises localized magnetically-coupled, radio frequency (RF)-induced hyperthermia mediated by a material which is non-toxic to and, preferably, inert to or compatible with animal tissue and has incorporated therewithin iron-containing crystals of such size, amount, composition, and magnetic properties to impart a coercive force of at least 200 oersteds to the material, and wherein the frequency of the magnetic field is sufficiently low that essentially only magnetic hysteresis heating of the mediating material can occur.

The mediating or suscepting material is preferably a glass, glass-ceramic, or sintered ceramic with base compositions in the borate, phosphate, or silicate field and having incorporated therewithin iron-containing crystals of magnetite and/or a ferrite selected from the group of lithium, cobalt, nickel, manganese, and barium ferrite. Most preferably, the frequency of the RF magnetic field will not exceed about 10 kilohertz.

That patent discussed previous attempts to treat carcinomata through localized hyperthermia. Thus, early workers had implanted powdered magnetic materials, identified by those workers to be magnetic $Fe_2O_3$, into tissue and those particles became heated when coupled to a magnetic field through their dielectric and hysteresis losses. Those studies employed RF magnetic fields having frequencies of about 0.12–2 megahertz. Although those experiments demonstrated the operability of that method for heating tissue, two adverse concomitant effects precluded its acceptance as a useful modality for treating carcinomata. First, iron oxide in substantial concentrations tends to be toxic to and/or rejected by the body. Second, and more importantly, the normal tissue surrounding the tumor became too hot during exposure to the magnetic field and was subject to necrosis. This second effect was due to dielectric or eddy-current heating, i.e., heating resulting from ionic conductivity of body tissue and fluids.

It had been recognized that more disparate heating between the suscepted region and the surrounding tissue could be achieved if the excitation field was of lower frequency. Thus, the heating of normal tissue via dielectric or eddy-current heating, (a function of the square of the product of field and frequency) would be minimized, whereas magnetic hysteresis heating, which varies linearly with field frequency, would be maximized.

The patentees disclosed materials or compositions which exhibited magnetic properties which maximize hysteresis loss, i.e., they exhibited high magnetization, good coercivity, and high loop squareness, each of those properties contributing to hysteresis heating. That combination of properties permitted the use of RF frequencies of sufficiently low levels that essentially only magnetic hysteresis heating of the suscepting material could occur; dielectric or eddy-current heating effects being reduced to a negligible level.

The preferred embodiments of the invention contemplated encapsulating magnetic iron-containing crystals consisting essentially of magnetite or a ferrite in a glass, glass-ceramic, or sintered ceramic matrix, the crystals having a diameter exceeding superparamagnetic size.

It is explained in that patent that temperatures within the range of about 41°–44° C. will cause necrosis of tumor tissue, whereas normal animal tissue is not destroyed until temperatures in the vicinity of about 48° C. are reached. It was observed, however, that brief exposures to temperatures up to 50° C. could be tolerated with very little necrosis of normal tissue. Such higher temperatures destroy tumor cells very quickly, thereby significantly reducing the time required for treatment. Accordingly, a series of pulses of RF magnetic energy can be utilized, the time of each pulse required to produce necrosis of tumor tissue, while having substantially no effect upon normal tissue, being readily determined empirically. Likewise, the concentration of mediating material having magnetic iron-containing crystals incorporated therein necessary to cause the desired hysteresis heating effect can also be readily determined empirically. Hence, the upper temperature of heating can be controllably regulated by suitably selecting the suscepting material and restricting the quantity thereof administered.

Localized hyperthermia can be accomplished in several ways. For example, an aqueous dispersion of the target material in very finely-divided form can be injected directly into a tumor and/or into normal tissue contiguous with the tumor. Subsequent exposure to the RF-induced magnetic field causes the target material to be heated.

In another method, an aqueous dispersion of the powdered suscepting target material is injected via intravenous or arterial routes at a site near or distal to the tumor. The flow of blood provides the transport to the site of the tumor. Assistance in moving the injected material may be engendered by guiding the passage with a magnet.

Where there is surgical exposure of a tumor, the target material can be injected into or applied onto the outside of the tumor. Hyperthermia will be induced through magnetic field induction heating prior to and/or after the incision has been closed. Hence, the treatment can comprise a series of exposures. The target material will desirably be inert or else harmlessly degraded by body fluids, the degradation taking place so slowly that the target material will remain at the site of the tumor for a significant length of time. This circumstance enables a succession of individual treatments with RF fields to be conducted to secure localized heating with only one implacement of mediating material.

Further, it is possible to derivatize the target particles with tumor specific ions or with antibodies and/or other similarly bioactive molecules directed against a tumor. This permits specific localization of the target material in and/or around the tumor. Stated differently, agents specific to a particular tumor can be attached directly to the target material or by the use of chelating or other coupling agents.

It is also possible to utilize the physical properties of tumors in localizing the target material in the areas thereof. As an illustration, tumors commonly exhibit pH values either in the range of about 3–4 or in excess of about 8.5. The pH of body fluids is about 7.4. Consequently, it is possible to design magnetic target materials which precipitate at the pH value manifested by a particular tumor. Thereupon, the precipitated material can be heated with the RF magnetic field.

Finally, in yet another method, the target material can be presensitized to have an affinity for a tumor species and thereafter can be delivered to the tumor site by injection, cannulation, magnetic guidance, and the like. Such presensitization may involve the surface of the target material or the bulk thereof. To illustrate, the target material can be etched and the pores filled with a sensitizing agent. Examples of such sensitizing agents include K/Mg for low pH tumors and gallium for lung carcinomata.

In summary, the basic consideration in the above patent was given to a RF range of frequencies and a field strength of a magnetic field to minimize eddy-current heating of normal tissue while hysteresis heating, due to the biocompatible, non-toxic suscepting target material, was taking place. Because of the dependence of the eddy-current heating on field and frequency [approximately $(wH)^2$], the working frequency was determined to be in the 10 kilohertz region or below with the field strength in the vicinity of 700 oersteds. The suscepting magnetic target material was required to develop sufficient power (watts/cm$^3$ of tissue) under the above field and frequency conditions to produce temperatures in the 41°–44° C. range, while not causing toxic or rejection problems within the body. Specific reference is made to that patent for further information regarding the treatment of tumors by hyperthermia.

Published U.K. Application GB No. 2,024,007A discloses a method for employing hyperthermia to kill cancer cells which contemplates two general steps:

First, minute particles of a ferromagnetic, diamagnetic, or paramagnetic material compatible with living tissue are introduced into the cancer cells, the sole ferromagnetic material mentioned being ferric hydroxide; and Second, the cancer cells and adjacent normal cells are subjected to a high frequency electromagnetic field, the field having a range of frequencies from 50 kilohertz to 10 megahertz and magnetic field strength of 400–800 oersteds, preferably 550–650 oersteds.

At least two fundamental aspects of that disclosure serve to differentiate it from that of U.S. Pat. No. 4,323,056, supra:

(1) U.S. Pat. No. 4,323,056 employs a RF magnetic field which has a frequency sufficiently low that essentially only magnetic hysteresis heating of the suscepting material can occur; and (2) U.S. Pat. No. 4,323,056 demands that the suscepting material be biocompatible, both chemically and physically, with normal animal tissue.

In contrast, the published application teaches the utilization of dielectric or eddy-current heating of the suscepting material in combination with hysteresis heating. As observed in U.S. Pat. No. 4,323,056 dielectric heating resulting from ionic conductivity of body tissue and fluids causes normal tissue adjacent to a tumor to become too hot, thereby leading to necrosis thereof. Furthermore, ferric hydroxide is known to be toxic to animal tissue.

In a literature article, "Potential Treatment of Cancer by Electromagnetic Heating", *Surgery, Gynecology and Obstetrics*, April, 1960, pages 499–500, R. K. Gilchrist refers to a report by one Medal (no citation of the report is provided) indicating that it is possible to cause local necrosis in tissue containing 0.005 gram of magnetic particles having diameters of 0.02–0.1 micron through exposure to a field of 1,500,000 volt-amperes, 450 oersteds, and 1.1 kilohertz. That exposure effects heating via hysteresis. The article, however, is principally concerned with eddy-current heating and inductothermy. There is no statement of any advantage to be gained in utilizing hysteresis heating instead of eddy-current heating and the publication concludes with the prediction that eventually hyperthermia will evolve to such an extent that target materials will not be necessary. Moreover, there is no statement as to the identity of any operable magnetic material. Yet, as pointed out in U.S. Pat. No. 4,323,056, iron oxide, the magnetic material most used in the prior hyperthermia work, is toxic to animal tissue. Consequently, where such is to be employed as the target material, U.S. Pat. No. 4,323,056 teaches enveloping it in a glass, glass-ceramic, or ceramic matrix.

U.S. Pat. No. 4,136,683 describes a three-step process for measuring the intracellular temperature of cells within an animal body:

(a) intracellularly injecting particles having a size less than 1 micron demonstrating ferromagnetic, paramagnetic or diamagnetic properties into the cells;

(b) determining the magnetic susceptibility of the intracellular particles; and then (c) correlating the measured magnetic susceptibility to corresponding temperature of the particles.

The patent has no disclosure regarding hyperthermia, i.e., the reduction of a cancerous mass via localized heating of cancerous cells. On the contrary, the patent simply seeks to measure the internal temperature of cells. Moreover, the patent indicates the effectiveness of any ferromagnetic, paramagnetic, or diamagnetic material. In contrast, the present invention requires the use of magnetic materials exhibiting very explicitly defined characteristics. Furthermore, the patent describes the use of a high frequency electromagnetic field, whereas the instant invention utilizes fields of relatively low frequencies. Finally, the patent makes no mention of encapsulating the magnetic particles within a material non-toxic to animal tissue.

U.S. Pat. No. 2,161,292 is concerned with a device for providing a more efficient means for transmitting electromagnetic radiations to an animal or human body to thereby subject the body to the influence of transmitted energy. The device consists of a dipole encapsulated within a ceramic member and is connected via wires to an oscillator generator, the ceramic member having a dielectric constant similar to that of the body to be treated. The shape of the ceramic member is so designed that the energy is transmitted therethrough to the body without passing through air. The patent indicates that air causes reflection phenomena which severely limit the amount of transmitted energy received by a body.

The patent does not disclose implanting a magnetic susceptor in an animal body. Furthermore, the patent does not teach the necessity for utilizing a susceptor material having iron-containing particles therein to impart a desired coercive force to the material. Finally, the patent makes no reference to a RF magnetic field or to hysteresis heating, both of those features constituting the heart of the instant invention.

U.S. Pat. No. 3,474,777 describes means for localizing a therapeutic agent at a particular treatment site within a body. That means contemplated three basic steps:

(a) forming microcapsules comprising the therapeutic agent in combination with a magnetically responsive substance;

(b) injecting the microcapsules into the body, e.g., into the blood stream; and then (c) directing the microcapsules to a desired site via the application of a magnetic field.

No reference whatever is made to hyperthermia. No mention is made of a RF magnetic field. There is no discussion of hysteresis heating.

None of the above three patents alone or any combination thereof can be deemed to teach the use of a mediating material having ferromagnetic particles incorporated therewithin which is non-toxic to animal tissue, coupled with the limitation that heating will be essentially confined to hysteresis heating.

BRIEF DESCRIPTION OF THE DRAWINGS

FIG. 5 is a graph reporting threshold values of electrical irritation of a magnetic field at various frequencies witnessed by a human torso, along with curves corresponding to the delivery of one watt/gram of heat treated and non-heat treated samples of an operable glass-ceramic material.

DESCRIPTION OF THE INVENTION

Further investigation has revealed major constraints on the safe application of the frequency/field values described in U.S. Pat. No. 4,323,056 which involves the induced electric field within an animal body produced by the time-varying magnetic field. Thus, whereas this induced emf is responsible for eddy-current heating, it produces another effect of critical significance in animal bodies, viz., the actuation of nerve and muscle response. This response is equivalent to electrical shock and, as such, represents electromagnetic toxicity. Manifestations of this toxicity include the potential induction of cardiac arrhythmia with possible cardiac arrest, as well as the potential induction of central nervous system dysfunction including seizure.

Therefore, the primary objective of the present invention was to improve upon the method disclosed in U.S. Pat. No. 4,323,056 through the application of a magnetic field which not only will subject the mediating material to essentially only hysteresis heating, but also which is designed such that the nerve and muscle response of the animal body to the induced emf is substantially decreased.

Investigations were conducted to acquire what have been termed "irritation threshold" values of a magnetic field at various frequencies employing the humand hand and finger as the probes. In those studies, the sensation threshold was determined empirically by the onset and persistence of numbing or tingling of the hand (shock).

When those data were scaled to estimate human torso "irritation thresholds", it was determined that the field and frequency requirements cited in U.S. Pat. No. 4,323,056 were inappropriate for all but the smallest non-human subjects which, therefore self-evidently, created very substantive constraints on the practice of that patent.

Figure 1:
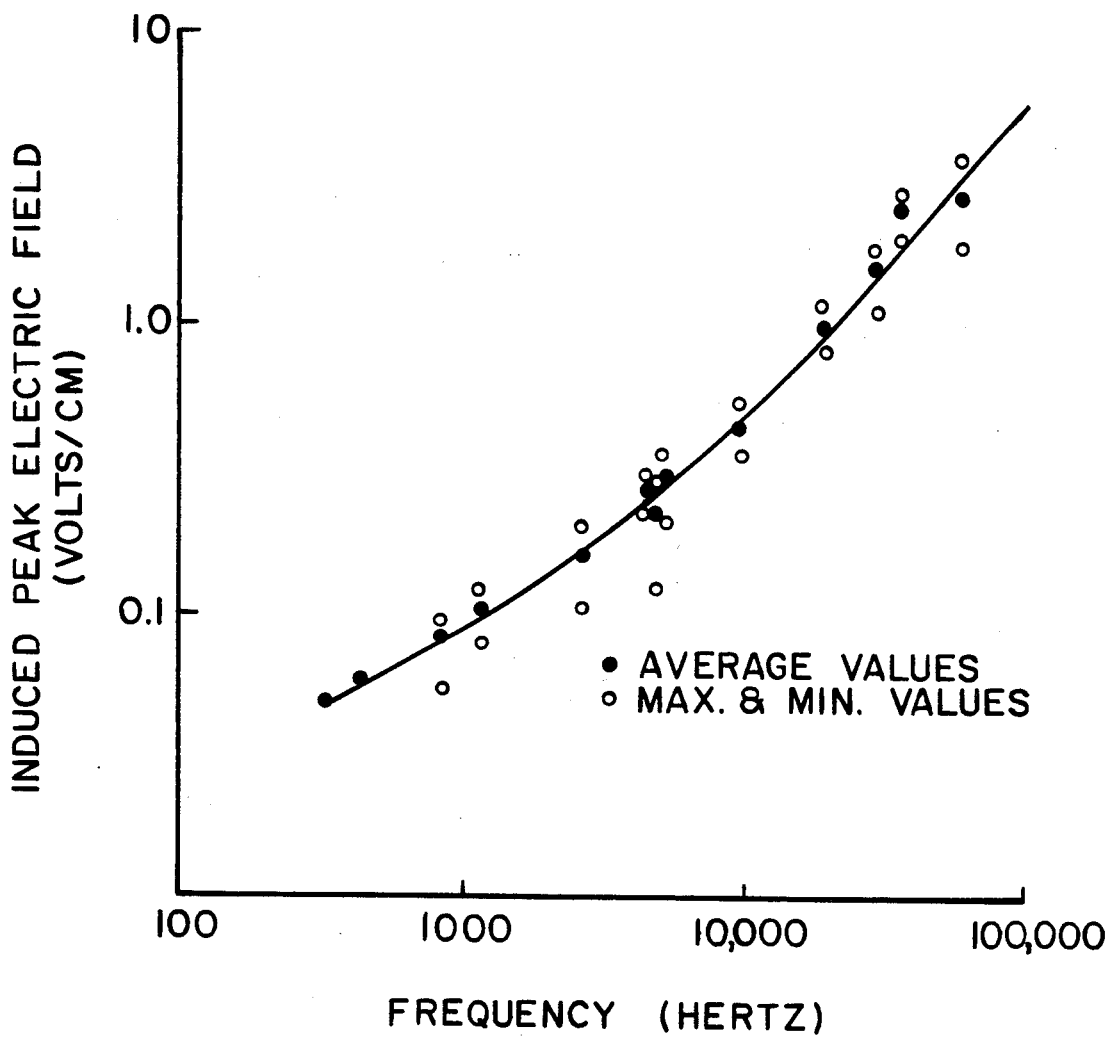
FIG. 1 is a graph depicting threshold values of electrical irritation of a magnetic field at various frequencies.
Figure 2:
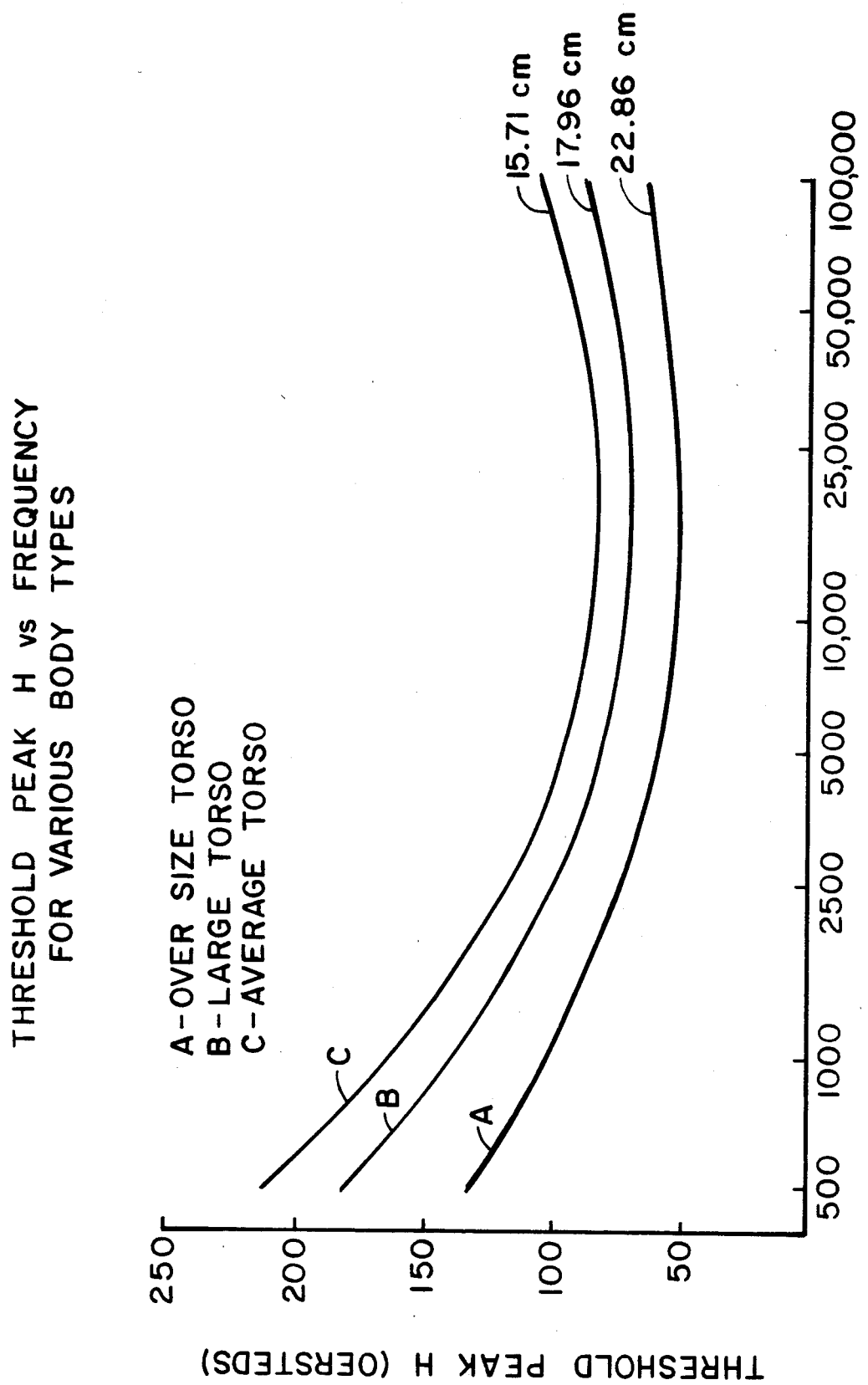
FIG. 2 is a graph recording threshold values of electrical irritation of a magnetic field at various frequencies for three body types and positions for an elliptical solenoidal coil.

These data are illustrated in the appended graph comprising FIG. 1 wherein the ordinate reflects the induced electric field, reported in terms of volts/cm, and the abscissa records the frequency in terms of hertz. The use of electric field strength, instead of magnetic field strength, was considered more appropriate because it normalizes the data independent of the size of the hand. The average values of threshold are plotted as a function of frequency as well as the maximum and minimum values within the sample set. Utilizing the data in this form permits the calculation of the threshold magnetic field for any enclosed path within the body and for any field distribution within a specific coil geometry. As an example of such calculation, appended FIG. 2 records the threshold magnetic field/frequency values for three body types and positions for an elliptical solenoid coil. The average radius of each body is reported.

The actuation of nerve and muscle by an applied electric field is well known. In addition, recent studies have shown the phenomenon as a function of frequency. The frequency response (magnetic field induced emf) has the same characteristic as that reported in the literature for electric field (C. F. Dalziel et al., "Effect of Frequency in Let-go Currents", *AIEE Trans.*, 62, 745–750, 1943).

The basic import of these data is to illustrate the field/frequency region available for hysteresis heating of the human body which would be free from electrical irritation and undue body heating resulting from eddy currents. Accordingly, these data represent a method to define the electromagnetically-safe operational limits for the induction of hysteresis heating in subjects of various sizes.

As can be observed from the FIGURES, electrical irritation is the field limiting constraint at the low frequency end, whereas, at the high frequency end, eddy-current heating to the whole body restricts the field. It should be noted that some degree of overall body heating may be useful to which hysteresis heating is added in the suscepted region.

Figure 3:
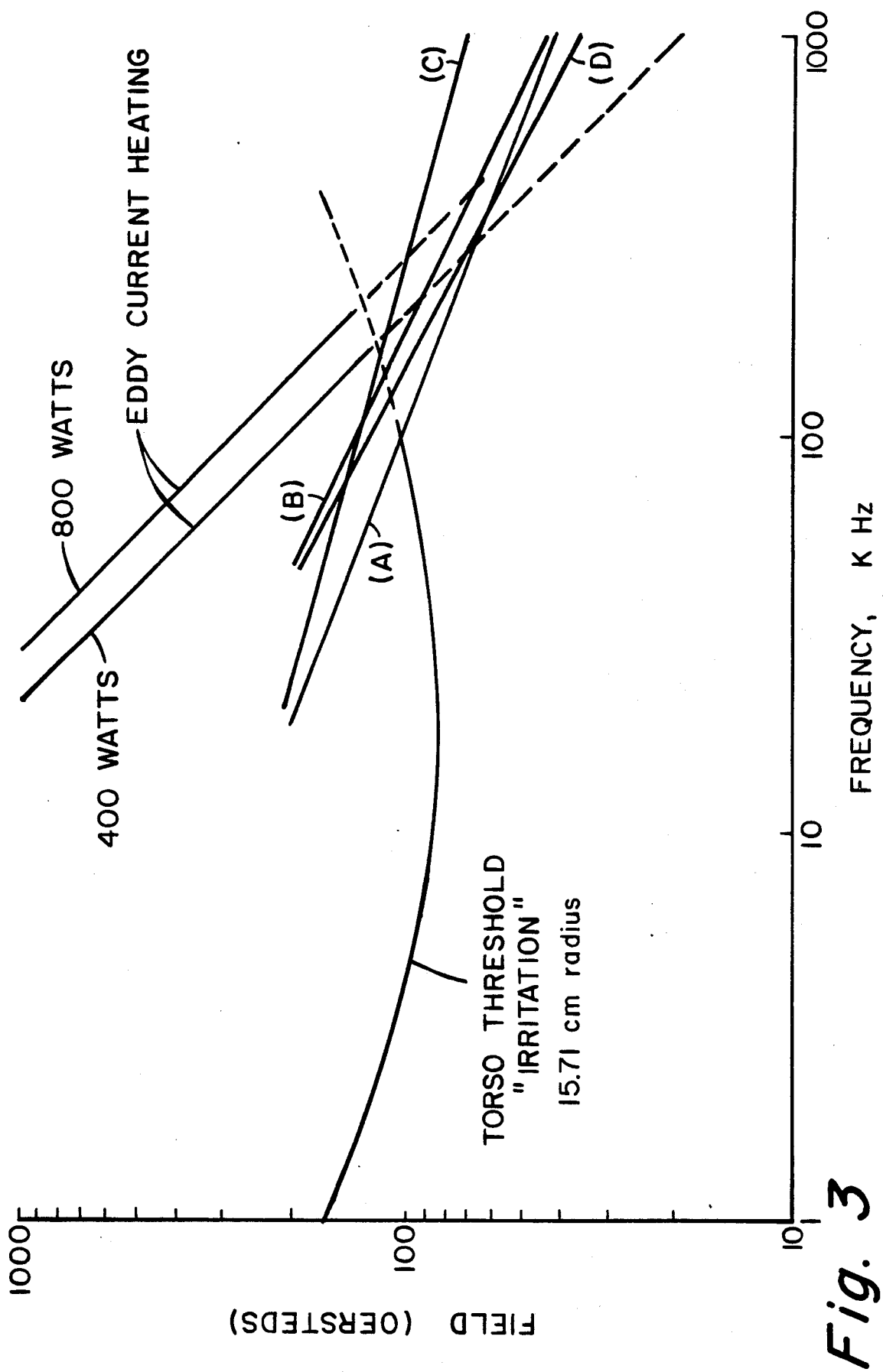
FIG. 3 is a graph recording threshold values of electrical irritation of a magnetic field at various high frequencies experienced by a human torso along with eddy current heating curves for 400 watts and 800 watts, and curves corresponding to the delivery of one watt/gram of three representative operable glass-ceramic materials and magnetite.
Figure 4:
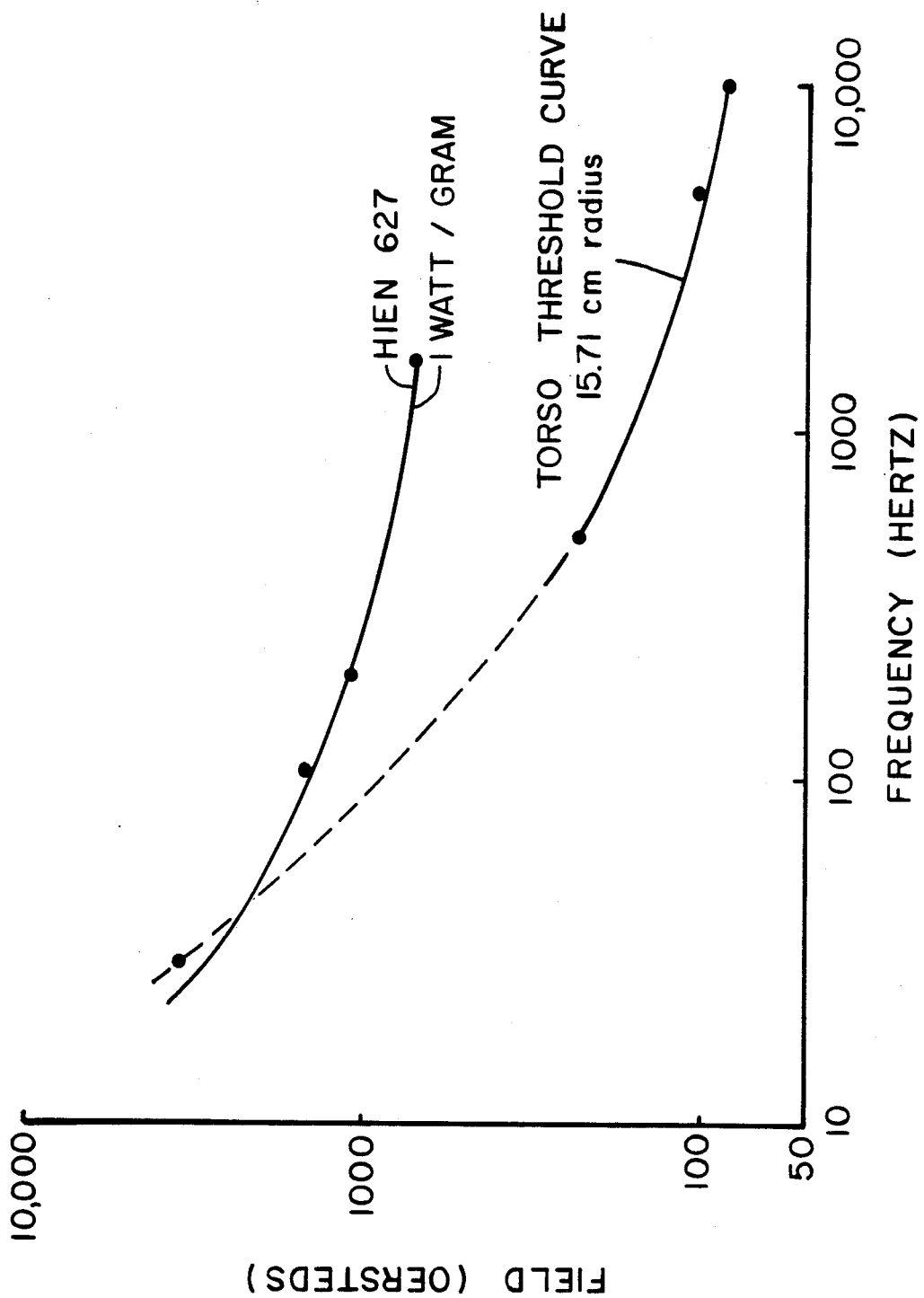
FIG. 4 is a graph recording threshold values of electrical irritation of a magnetic field at various low frequencies experienced by a human torso, and a curve representing the delivery of one watt/gram of a commercially-marketed ferrite material.

This irritation effect must be considered in the selecting of the material to be implanted which is relevant to the safe field/frequency regime, as depicted in FIG. 3 for high frequency range and FIG. 4 for low frequency range. Stated in another way, the character of the magnetic properties demonstrated by the material must conform to the safe frequency regime. For example, safe operation in the high frequency region (greater than 10 kilohertz and ranging up to 600 kilohertz) demands a low applied field, viz., at least 20 but less than about 200 oersteds. Therefore, the coercivity of the mediating material will most preferably be correspondingly low, viz., about one-third the level of the applied field, in order to open the high frequency loop sufficiently to produce optimum hysteresis heating. In sharp contrast, operation in the desirable region of the low frequency range (less than about 40 hertz) mandates a high applied field, viz., at least about 2000 oersteds which, in turn, demands that the suscepting material exhibit high coercivity to develop sufficient heating power.

Work with implanted ceramics having encapsulated therein iron-containing, magnetic crystals of magnetite and/or a ferrite in tumor-bearing mice indicated that a value of heating of one watt per gram of material was sufficient to obtain the necessary kill temperature of about 41°–44° C. Thus, cure rates for subcutaneous tumors in mice treated with sufficient ceramic, developing one watt per gram of ceramic, have been obtained as high as 50%. For larger animals, depending upon the location and size of the tumor, it has been postulated that the implanted material should also have a heating value of about one watt per gram. It has been demonstrated that this ceramic heating value would deliver adequate therapeutic tumor hyperthermia irrespective of location, when the tumor is surrounded by a ceramic shell of 1 mm thickness.

The limitations placed upon the magnetic field in any frequency regime to minimize the concomitant electrical shock hazard impose a limit on the heating value (watts/gram) achievable in the above-described glass, glass-ceramic, and sintered ceramics having ferromagnetic particles incorporated therewithin. Since it has been demonstrated that a heating value on the order of 1 watt/gram is sufficient for therapeutic hyperthermia, the usable safe field of the present practice frequency regimes is outside of, and narrowly defined, when compared with the disclosure of U.S. Pat. No. 4,323,056.

The torso "irritation threshold" curve has been replotted in the appended FIG. 3 for the high frequency regime and in FIG. 4 for the low frequency regime. In FIG. 4, the solid portion of the threshold curve represents measured values and the dotted portion estimated values calculated from the Dalziel et al. literature reference above. Values of induced electric field and frequency falling below the threshold lines for each curve will not produce electrical irritation. Eddy current heating curves for 400 watts and 800 watts are also drawn in FIG. 3. These lines delineate other constraints which must be observed with regard to a safe operating region in the higher frequency regime. Hence, in FIG. 3 the area below the irritation curve and to the left of the appropriate eddy current heating line represents the desired irritation-free region. In FIG. 4 the area below the curve represents the irritation-free region.

This circumstance augurs the proposition that there will always be two regimes of frequencies wherein the electrical irritation effect and eddy current heating can be controlled to tolerable levels; viz., a low frequency range below about 1 kilohertz and a high frequency region above about 100 kilohertz. The selection of the frequency interval utilized will be grounded on such other factors as the chemical and physical properties of the materials with regard to their being implanted in human tissue. Where field strengths below about 100 oersteds are employed, it appears that all frequencies are available for use with essentially no potential for irritation.

The following table records the compositions of several glasses, expressed in terms of weight percent on the oxide basis, operable in the instant invention. Examples 1 and 3 are reported as analyzed, all of the iron present being expressed in terms of $Fe_2O_3$. Example 2 is tabulated as calculated from the batch ingredients utilized, all of the iron being reported as $Fe_3O_4$. No $B_2O_3$ was purposefully included in the batch of Example 1, the amount determined via analysis comprising impurities present in the batch components. The actual batch constituents employed were either oxides or other compounds which, when melted together, were converted into the desired oxides in the proper proportions.

In each composition the batch materials were compounded, thoroughly mixed together to assist in achieving a homogeneous melt, run into platinum crucibles, lids placed upon the crucibles, and the crucibles then introduced into a furnace operating at about 1400°–1500° C. After about 1–4 hours, the crucibles were withdrawn from the furnace, the lids removed therefrom, and the melts drigaged; i.e., poured as a relatively fine stream into a bath of water to form small particles of glass.

The glass particles were thereafter subjected to the heat treatments reported in the table to cause the development of magnetic, iron-containing crystals therein. X-ray diffraction analysis posited the major crystal phase in Example 1 to be lithium ferrite, theorized to have the stoichiometry of $LiFe_3O_8$, that conclusion being deduced from a slight shift observed in the normal $Fe_3O_4$ peak. X-ray diffraction analysis of Example 2 indicated the predominant crystal phase to be magnetite and that of Example 3 to be a manganese ferrite. The table also reports the heating values demonstrated by the crystalline products expressed in terms of calories/loop/gram ($\times 10^{-5}$), as measured by calorimetric techniques. These latter data should be deemed to be illustrative only and merely serving to exhibit the capability of improving the heating values manifested by various compositions by applying different heat treatments thereto.

TABLE

|  | 1 | 2 | 3 |
|---|---|---|---|
| $SiO_2$ | 16.10 | 56.0 | 7.2 |
| $B_2O_3$ | 0.31 | 7.0 | 20.8 |
| $Al_2O_3$ | 12.90 | 5.0 | — |
| $Li_2O$ | 11.97 | — | — |
| $P_2O_5$ | 24.98 | — | — |
| MgO | 3.20 | — | 16.2 |
| $Fe_2O_3$ | 30.54 | — | 38.5 |
| $Na_2O$ | — | 4.0 | — |
| CaO | — | 3.0 | — |
| $ZrO_2$ | — | 5.0 | — |
| ZnO | — | 2.0 | — |
| $Fe_3O_4$ | — | 20.0 | — |
| MnO | — | — | 15.6 |

| Example | Heat Treatment | cal/loop/gram (100 oersteds) | cal/loop/gram (200 oersteds) |
|---|---|---|---|
| 1 | 400° C. for 2.5 hours in air | $0.2 \times 10^{-5}$ | $1.3 \times 10^{-5}$ |
| 2 | 675° C. for 16 hours in air | $0.13 \times 10^{-5}$ | $0.52 \times 10^{-5}$ |
| 3 | 325° C. for 2.5 hours in $N_2$ | $0.09 \times 10^{-5}$ | $1.0 \times 10^{-5}$ |
| 1 | Not heat treated | $0.09 \times 10^{-5}$ | $0.5 \times 10^{-5}$ |

The above table clearly illustrates that the performance of the mediating materials can be modified in a substantial manner by varying the composition, thermal history, and/or heat treatment applied thereto. Hence, the hysteresis heating potential of the materials can be altered quite widely by changing and optimizing their composition and microstructure through modifications in heat treatments applied thereto, thereby permitting tailoring of their coercivity and magnetic moment.

Whereas Examples 1–3 represent "conventional" glass-ceramic material, i.e., bodies which are initially formed as glasses and subsequently crystallized in situ via heat treatment to glass-ceramics, it will be appreciated that any material having ferromagnetic particles incorporated therein may be operable in the inventive process.

Thus, whereas iron-containing crystals constitute the most likely and practical source of ferromagnetic particles because of their relative cheapness and easy accessibility, other materials exhibiting ferromagnetic properties which can be encapsulated so as to render them essentially non-toxic to, and preferably inert to and compatible with normal animal tissue are likewise operable. For example, platinum cobalt, manganese bismuth, and nickel cobalt alloys, and rare earth magnetic materials such as the samarium cobalt alloys, exhibit a level of ferromagnetic behavior recommending a special utility in the low frequency regime of the applicable field frequencies.

Furthermore, although glasses, glass-ceramics, and sintered ceramics have been deemed the most preferred materials for encapsulating the ferromagnetic particles, certain organic plastics, e.g., TEFLON ® FTP, possess the necessary inertness and non-toxicity to be suitable matrix materials.

FIG. 3 also records heating lines corresponding to the delivery of one watt/gram to three representative glass-ceramic materials, viz., Examples 1–3, and magnetite. The one watt/gram line for Example 1 (Curve A) indicates that the safe operating range for that material begins at a frequency of about 100 kilohertz. An examination of the one watt/gram line for Example 2 (Curve B) and the one watt/gram line for Example 3 (Curve C) shows that Example 2 enters the safe operating zone at about 140 kilohertz and Example 3 at about 150 kilohertz. Finally, the one watt/gram line for magnetite (Curve D) points out that Fe₃O₄ displays sufficient hysteresis heating in the field/frequency regime where there is minimal electrical irritation and no excessive extraneous eddy current heating, starting at about 100 kilohertz.

It can be calculated theoretically that the maximum amount of heating produced per gram of mediating material possessing optimum magnetic properties as a function of the applied field and frequency is defined in the expression $$Q(watts/gram) = 0.04(H_{app})^2 f \times 10^{-7}$$

where $H_{app}$ is the applied field in oersteds and f is the frequency in hertz. The expression "optimum magnetic properties" connotes that the magnetic phase manifests internally a large area loop behavior with a coercive field one-half that of the applied field.

Comparison of actual heating values at a given field strength and frequency with the theoretical maximum provides a means to rate the performance of a particular material. This phenomenon is depicted in FIG. 5 where the one watt/gram curves for samples of Example 1 which had been heat treated in accordance with the above table and non-heat treated samples are drawn for comparison. The significant changes in magnetic properties and concomitant heating values imparted via heat treatment are clearly evident since the curve representing the treated sample (Curve E) is substantially closer to the theoretical maximum curve (Curve G), as derived from the above expression, than Curve F, representing the untreated sample. Thus, Curve G reflects a material demonstrating optimum magnetic properties. These comparisons unequivocally evidence that the magnetic properties of a material can be modified via heat treatment thereof.

To illustrate the phenomenon in the low frequency regime, FIG. 4 records the irritation threshold curve and the one watt/gram heating line for a commercially available ferrite material, viz., HIEN627 marketed by Hercules, Inc., Wilmington, Del. As can be observed, the HIEN material enters the irritation-free zone at about 40 hertz and 2400 oersteds.

In general, the present inventive method requires a mediating or suscepting material which is essentially non-toxic to, and preferably inert to, compatible with, and/or degradable in time within animal tissue, and which has incorporated therewithin ferromagnetic particles of such size, composition, concentration, and ferromagnetism that, when subjected to the appropriate magnetic field and frequency, the suscepting material will be heated sufficiently, by hysteresis heating only, to raise the temperature of a contiguous tumor to about 41°–44° C. The suscepting material can be tailored to exhibit the desired magnetic properties through the addition of compositional dopants and/or via modifications in thermal history and/or heat treatment.

The ultimate choice of the field frequency to be utilized will depend upon such factors as mentioned above concerning the nature of the suscepting material. To be most useful, the particle size of the mediating material will be very small, no more than a few microns at most and preferably smaller, and controlled within certain limits. Where the ferromagnetic particles are encapsulated within a glass, glass-ceramic, sintered ceramic particle, or other biocompatible, organic or inorganic encapsulant, it is quite apparent that the crystals will be of a smaller diameter than the particles.

In like manner to the description provided in U.S. Pat. No. 4,323,056, supra, the mediating material will be essentially non-toxic to, and preferably inert to or compatible with, animal tissue, and the ferromagnetic particles will, by their size and ferromagnetic range, have the necessary hysteretic response. The methods for achieving localized hyperthermia described in that application are equally applicable in the present inventive method.

"Indirect Heating Source for Treatment of Malignant Brain Tumours", Philip C. Thackray, Zvi H. Meiksin, Sidney K. Wolfson, and Rober G. Selker, *Electrocomponent Science and Technology*, 1, 91–96 (1974), describes apparatus for use in inducing hyperthermia in brain carcinomata. The authors discuss the use of implanted low carbon steel particles as the source of heating and note the desirability of utilizing hysteresis heating. The use of steel particles, however, cannot be tolerated in the present inventive method because of the inherent toxicity thereof.

We claim:

1. In a method for reducing the mass of a tumor in animal tissue through localized, magnetically-coupled, RF-induced hyperthermia comprising the steps of:
   (a) implanting a particulate material into the tumor and/or into normal tissue immediately adjacent to the tumor, which material is essentially non-toxic to, and inert to or compatible with normal animal tissue, and which has incorporated therewithin ferromagnetic particles; and (b) applying a magnetic field to subject said material to essentially only hysteresis heating to raise the temperature of said tumor to between about 41°–44° C.;

the improvement which comprises:

applying a magnetic field to said material of at least about 20, but less than 200 oersteds, at a frequency greater than 10 kilohertz and ranging up to about 600 kilohertz, the particles incorporated within said material being of such size, composition, concentration, and ferromagnetic properties to develop a heating value up to about one watt/gram of said material, such that nerve and muscle response of said animal to the induced emf is minimized.

2. A method according to claim 1 wherein said material is selected from the group of glasses, glass-ceramics, and sintered ceramics.

3. A method according to claim 1 wherein said ferromagnetic particles are selected from the group of iron-containing crystals, platinum cobalt, manganese bismuth, and nickel cobalt alloys, and rare earth metal magnetic alloys.

4. A method according to claim 3 wherein said iron-containing crystals are selected from the group of magnetite and a ferrite.

5. A method according to claim 1 wherein said material is tailored to exhibit desired ferromagnetic properties by varying at least one factor selected from the group of composition, thermal history, and heat treatment applied thereto.

6. A method according to claim 1 wherein said material exhibits a coercivity of about one-third that of said applied field.

7. In a method for reducing the mass of a tumor in animal tissue through localized, magnetically-coupled, RF-induced hyperthermia comprising the steps of:

(a) implanting a particulate material into the tumor and/or into normal tissue immediately adjacent to the tumor, which material is essentially non-toxic to, and inert to or compatible with normal animal tissue, and which has incorporated therewithin ferromagnetic particles; and (b) applying a magnetic field to subject said material to essentially only hysteresis heating to raise the temperature of said tumor to between about 41°–44° C.;

the improvement which comprises:

applying a magnetic field to said material of at least about 2000 oersteds and a frequency below about 40 hertz, the particles incorporated within said material being of such size, composition, concentration, and ferromagnetic properties to develop a heating value up to about one watt/gram of said material, such that nerve and muscle response of said animal to the induced emf is minimized.

8. A method according to claim 7 wherein said material is selected from the group of glasses, glass-ceramics, and sintered ceramics.

9. A method according to claim 7 wherein said ferromagnetic particles are selected from the group of iron-containing crystals, platinum cobalt, manganese bismuth, and nickel cobalt alloys, and rare earth metal magnetic alloys.

10. A method according to claim 9 wherein said iron-containing crystals are selected from the group of magnetite and a ferrite.

11. A method according to claim 7 wherein said material is tailored to exhibit desired ferromagnetic properties by varying at least one factor selected from the group of composition, thermal history, and heat treatment applied thereto.

* * * * *